(12) United States Patent
Jasserand et al.

(10) Patent No.: US 6,407,106 B1
(45) Date of Patent: Jun. 18, 2002

(54) N-TRIAZOLYLMETHYL-PIPERAZINE COMPOUNDS WITH NEUROKININ-RECEPTOR ANTAGONIST ACTIVITY

(75) Inventors: Daniel Jasserand, Hannover; Uwe Schoen, Burgdorf; Holger Sann; Reinhard Brueckner, both of Hannover; Christian Eeckhout, Lindwedel, all of (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/915,558

(22) Filed: Jul. 27, 2001

(30) Foreign Application Priority Data

Jul. 28, 2000 (DE) .......................................... 100 36 818

(51) Int. Cl.[7] .................. A61K 31/5377; C07D 413/14
(52) U.S. Cl. .................... 514/235.2; 540/575; 544/121; 544/230; 544/295; 544/357; 544/364; 544/366
(58) Field of Search ................................ 544/121, 366; 514/235.2

(56) References Cited

U.S. PATENT DOCUMENTS

| 5,670,505 A | 9/1997 | Matsuo et al. |
| 5,883,098 A | 3/1999 | Matsuo et al. |
| 6,001,833 A | 12/1999 | Jesserrand |

FOREIGN PATENT DOCUMENTS

| EP | 0655442 | 5/1995 |
| EP | 0899270 | 3/1999 |
| WO | 9722597 | 6/1997 |
| WO | 9857954 | 12/1998 |
| WO | WO9857954 | 12/1998 |

OTHER PUBLICATIONS

Y. Takeda, "Molecular Cloning, Structural Characterization and Functional Expression of the Human Substance P Receptor" Biochemical and Biophysical Research Communications, vol. 179, No. 3, 1991.

Nadia M.J. Rupniak, "Differential inhibition of foot tapping and chromodacryorrhoea in gerbils by CNS penetrant and non–poenetrant tachykinin $NK_1$ receptor antagonists" European Journal of Pharmacology 265, 1994.

Klaus Banert, "Basenkatalysierte Bildung von Allenylaziden aus Propargylaziden: Neue Synthesen fur 1,2, 3–Triazole" Chemistry Ber. 1989.

*Primary Examiner*—Robert W. Ramsuer
(74) *Attorney, Agent, or Firm*—Crowell & Moring LLP

(57) ABSTRACT

N-triazolylmethyl-piperazine compounds which exhibit neurokinin receptor antagonistic activity corresponding to the formula I:

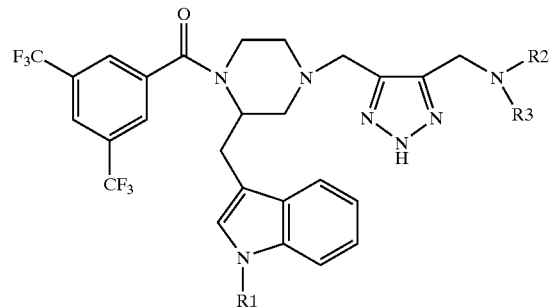

wherein
$R^1$, $R^2$ and $R^3$ have the meanings given in the specification; pharmaceutical compositions containing these compounds; a process for preparing these compounds, and intermediate products of this process.

8 Claims, No Drawings

N-TRIAZOLYLMETHYL-PIPERAZINE COMPOUNDS WITH NEUROKININ-RECEPTOR ANTAGONIST ACTIVITY

BACKGROUND OF THE INVENTION

The present invention relates to novel 2-indolylmethyl-piperazine derivatives which are antagonistic to neurokinin receptors and which are substituted at a nitrogen of the piperazine parent structure by a triazolylmethyl radical. Furthermore, the invention relates to medicaments containing these novel N-triazolylmethyl-piperazine derivatives. Furthermore, the invention relates to a process for the preparation of the novel piperazine derivatives and also intermediate products of this process.

Compounds which are structurally similar to the compounds of the present invention are already known from WO 98/57954, which compounds are ascribed general properties which are antagonistic to tachykinin, neurokinin A or alternatively neurokinin B and which are capable of influencing the central nervous system (=CNS).

2-Indolylmethyl-piperazine derivatives having a different substitution pattern from the compounds of the present invention and which have properties which are antagonistic to neurokinin receptors are described in EP 0 899 270 A1.

Furthermore, additional 2-indolylmethyl-piperazine derivatives having a different substitution pattern from the compounds of the present invention are known from EP 0 655 442 A1 which are ascribed properties which generally are antagonistic to tachykinin, neurokinin A or alternatively neurokinin B and which are regarded as being suitable to influence the CNS.

SUMMARY OF THE INVENTION

It was an object of the present invention to provide novel active substances having properties antagonistic to neurokinin (=NK) receptors.

Another object of the invention was to provide compounds with neurokinin receptor antagonistic properties and an improved activity profile.

A further object of the invention was to provide compounds with neurokinin receptor antagonistic properties which are suitable for treating peripheral disturbances such as functional and inflammatory disturbances of the gastrointestinal tract.

These and other objects of the invention have been achieved by providing a compound corresponding to the formula I:

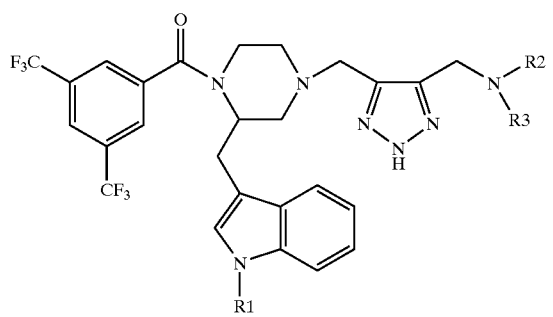

wherein
$R^1$ is hydrogen or lower alkyl,
$R^2$ is lower alkyl, di-lower-alkylamino lower alkyl, lower-alkoxycarbonyl lower alkyl; cyclo(hetero)alkyl having 5–6 ring atoms, which may optionally be substituted once or twice by lower alkyl and which optionally contains 1–2 double bonds; (hetero)phenyl lower alkyl optionally substituted once or twice in the (hetero)phenyl ring by halogen, lower alkyl and/or lower alkoxy, the lower-alkyl chain of which (hetero)phenyl lower alkyl is optionally substituted once or twice by lower alkyl or by spiro-$C_4$–$C_5$-alkylene; or phenyl lower alkoxy optionally substituted once or twice in the phenyl ring by halogen, lower alkyl and/or lower alkoxy, and $R^3$ is lower alkyl, lower-alkoxycarbonyl lower alkyl or cyclo(hetero)alkyl with 5–6 ring atoms which is optionally substituted once or twice by lower alkyl, or $R^2$ and $R^3$, together with the nitrogen to which they are bonded, form a cyclic group of formula a:

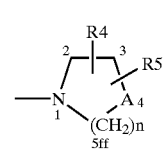

wherein
A is nitrogen, oxygen, methylene or methylidene, the double bond of which, together with the adjacent carbon, is formed in position 3 of group a,
n is a whole number from 1 to 3,
$R^4$ is hydrogen, lower alkyl, lower-alkoxy lower alkyl, lower alkoxycarbonyl, lower-alkoxycarbonyl lower alkyl, di-lower-alkylamino lower alkyl; (hetero)phenyl optionally substituted once or twice by halogen, lower alkyl and/or lower alkoxy; (hetero)phenyl lower alkyl optionally substituted once or twice in the (hetero)phenyl ring by halogen, lower alkyl and/or lower alkoxy, the lower-alkyl chain of which (hetero)phenyl lower alkyl is optionally substituted once or twice by lower alkyl; cyclo(hetero)alkyl with 5–6 ring atoms, or cyclo(hetero)alkyl lower alkyl, the cyclo(hetero)alkyl group of which has 5–6 ring atoms, and
$R^5$ is hydrogen, lower alkyl or lower-alkoxy lower alkyl, or
$R^4$ and $R^5$ together are spiroethylenedioxy bonded to a carbon of group a; $C_3$–$C_4$-alkylene bonded to two adjacent atoms of group a; or phenyl fused via two adjacent carbons of group a, or
$R^2$ and $R^3$, together with the nitrogen to which they are bonded, form a pyrrolidine ring which is substituted twice by $C_4$-alkylene which is bonded each time via two adjacent carbon atoms;
or a physiologically compatible acid addition salts thereof.

It has now surprisingly been discovered that one group of novel N-triazolylmethyl-piperazine derivatives is distinguished by specific properties antagonistic to NK-1 receptors and exerts its action preferentially in the peripheral region. Accordingly, the group of compounds according to the invention appears particularly suitable for the treatment of peripheral disturbances induced by NK-1, in particular for the treatment of functional and inflammatory disturbances of the gastrointestinal tract.-

The invention thus relates to new compounds corresponding to the formula I:

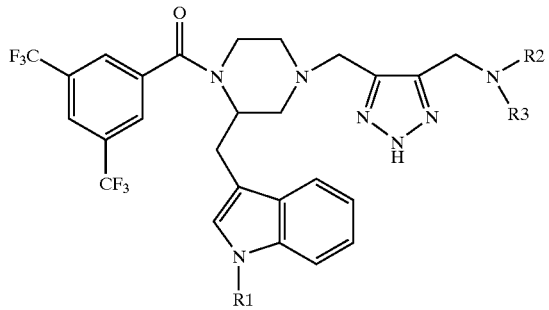

wherein
- $R^1$ is hydrogen or lower alkyl,
- $R^2$ is lower alkyl, di-lower-alkylamino lower alkyl, lower-alkoxycarbonyl lower alkyl; cyclo(hetero)alkyl having 5–6 ring atoms, which may optionally be substituted once or twice by lower alkyl and which optionally contains 1–2 double bonds; (hetero)phenyl lower alkyl optionally substituted once or twice in the (hetero) phenyl ring by halogen, lower alkyl and/or lower alkoxy, the lower-alkyl chain of which (hetero)phenyl lower alkyl is optionally substituted once or twice by lower alkyl or by spiro-$C_4$–$C_5$-alkylene; or phenyl lower alkoxy optionally substituted once or twice in the phenyl ring by halogen, lower alkyl and/or lower alkoxy, and
- $R^3$ is lower alkyl, lower-alkoxycarbonyl lower alkyl or cyclo(hetero)alkyl with 5–6 ring atoms which is optionally substituted once or twice by lower alkyl, or
- $R^2$ and $R^3$, together with the nitrogen to which they are bonded, form a cyclic group of formula a:

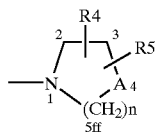

wherein
- A is nitrogen, oxygen, methylene or methylidene, the double bond of which, together with the adjacent carbon, is formed in position 3 of group a, n is a whole number from 1 to 3,
- $R^4$ is hydrogen, lower alkyl, lower-alkoxy lower alkyl, lower alkoxycarbonyl, lower-alkoxycarbonyl lower alkyl, di-lower-alkylamino lower alkyl; (hetero) phenyl optionally substituted once or twice by halogen, lower alkyl and/or lower alkoxy; (hetero) phenyl lower alkyl optionally substituted once or twice in the (hetero)phenyl ring by halogen, lower alkyl and/or lower alkoxy, the lower-alkyl chain of which (hetero)phenyl lower alkyl is optionally substituted once or twice by lower alkyl; cyclo(hetero) alkyl with 5–6 ring atoms, or cyclo(hetero)alkyl lower alkyl, the cyclo(hetero)alkyl group of which has 5–6 ring atoms, and
- $R^5$ is hydrogen, lower alkyl or lower-alkoxy lower alkyl, or
- $R^4$ and $R^5$ together are spiroethylenedioxy bonded to a carbon of group a, $C_3$–$C_4$-alkylene bonded to two adjacent atoms of group a, or phenyl fused via two adjacent carbons of group a; or
- $R^2$ and $R^3$, together with the nitrogen to which they are bonded, form a pyrrolidine ring which is substituted twice by $C_4$-alkylene which is bonded each time via two adjacent carbon atoms, and physiologically compatible acid addition salts of compounds of Formula I.

Furthermore, the invention also relates to pharmaceutical compositions containing the compounds of Formula I.

In addition, the invention relates to a process for preparing the compounds of Formula I and intermediate products of this process.

Whenever in the compounds of Formula I the substituents are or contain lower alkyl or alkoxy groups, these may be straight-chain or branched and contain 1 to 4 carbon atoms.

Whenever the substituents contain halogen, in particular fluorine, chlorine or bromine, preferably fluorine or chlorine, are used.

Whenever the substituents of the compounds of Formula I are or contain cyclo(hetero)alkyl, this may be a pure carbocyclic group, or it may also represent carbocyclic compounds in which in each case 1 to 3 ring carbon atoms are replaced by nitrogen, oxygen and/or sulfur. Nitrogen and oxygen are preferred heteroatoms.

Whenever the substituents of the compounds of Formula I are or contain (hetero)phenyl, this may stand for phenyl, or may also represent phenyl wherein in each case 1 to 3 ring carbon atoms are replaced by nitrogen.

Whenever the substituents of the compounds of Formula I are or contain (hetero)phenyl, this stands for phenyl in which in each case 1 to 3 ring carbon atoms are replaced by nitrogen.

$R^1$ preferably stands for hydrogen. Where $R^1$ stands for lower alkyl, methyl is preferred.

$R^2$ preferably stands for lower alkyl, in particular methyl, ethyl, isopropyl or tert. butyl; for di-lower-alkylamino lower-alkyl, in particular dimethylaminoethyl or dimethylamino-n-propyl; for lower-alkoxycarbonyl lower alkyl, in particular ethoxycarbonylmethyl; for cyclo(hetero) alkyl having 5 to 6 ring atoms, optionally substituted once by lower alkyl, in particular methyl, in particular for optionally substituted cyclopentyl, cyclohexyl or piperidinyl; for heterophenyl lower alkyl optionally substituted once or twice in the heterophenyl ring by lower alkyl, in particular methyl, or by lower alkoxy, in particular methoxy, in particular for optionally substituted pyridyl; or for phenyl-$C_2$–$C_4$-alkyl substituted once or twice in the phenyl ring by lower alkyl, in particular methyl, or by lower alkoxy, in particular methoxy.

$R^3$ preferably represents lower alkyl, in particular methyl, ethyl or isopropyl; or for lower-alkoxycarbonyl lower alkyl, in particular ethoxycarbonylmethyl.

Those compounds of Formula I wherein $R^2$ and $R^3$ are not simultaneously isobutyl are preferred.

Whenever $R^2$ and $R^3$, together with the nitrogen to which they are bonded, form a group of formula a, $R^4$ preferably stands for hydrogen; for lower alkyl, in particular methyl or isopropyl; for lower-alkoxy lower alkyl, in particular methoxymethyl; for lower-alkoxycarbonyl lower alkyl, in particular ethoxycarbonylmethyl; for di-lower-alkylamino lower alkyl, in particular dimethylaminoethyl; for (hetero) phenyl optionally substituted once by lower alkyl, in particular methyl, or by lower alkoxy, in particular methoxy, in particular for optionally substituted phenyl, pyridyl, pyrimidyl or pyrazolyl; for (hetero)phenyl lower alkyl optionally substituted once in the (hetero)phenyl ring by halogen, lower alkyl, in particular methyl, or by lower alkoxy, in particular methoxy, in particular for optionally substituted benzyl or pyridyl lower alkyl; for cyclo(hetero)alkyl having 5 to 6 ring atoms, in particular for cyclohexyl, pyrrolidinyl or piperidinyl; or for cyclo(hetero)alkyl lower alkyl, the cyclo(hetero)alkyl ring of which has 5 to 6 ring atoms, in particular for pyrrolidinyl-$C_1$–$C_2$-alkyl, morpholinoethyl or cyclohexylmethyl.

In any group of Formula a which may be present, $R^5$ preferably stands for hydrogen; for lower alkyl, in particular methyl; or for lower-alkoxy lower alkyl, in particular methoxymethyl.

Preferred compounds of Formula I are those in which in any group of Formula a which may be present, $R^4$ and $R^5$ are not bonded to the same atom of group a, with the exception of the preferred compounds of Formula I in which $R^4$ and $R^5$ together are spiroethylenedioxy bonded to a carbon of group a. Likewise, compounds of Formula I are preferred in which $R^4$ and $R^5$ are $C_3$–$C_4$-alkylene bonded to two adjacent ring atoms of group a.

In any group of Formula a which may be present, n stands for a whole number from 1 to 3. Where $R^4$ and $R^5$ are both hydrogen and at the same time A stands for methylene, n preferably stands for 2 or 3.

Generally, the substituents $R^4$ and $R^5$ of group a may be bonded to each ring atom of the group, including the ring atoms formed by A, which do not stand for oxygen. Where a ring atom of group a is substituted by $R^4$ or $R^5$, $R^4$ or $R^5$ replaces a hydrogen atom otherwise present at the same place, so that the usual valencies of the ring atoms of group a are retained. Where A stands for methylidene, the double bond thereof is preferably formed with the adjacent carbon in position 3 of group a, which in this case likewise forms a methylidene group.

Preferred are compounds of Formula I, in which an optionally present group a stands for pyrrolidine substituted by $R^4$ and $R^5$, wherein $R^4$ and $R^5$ are not both simultaneously hydrogen, or wherein an optionally present group a stands for 2,5-dihydropyrrole, piperidine, piperazine, morpholine or diazepan, each substituted by $R^4$ and $R^5$.

Particularly preferred is the compound (2R)-1-[3,5-bis(trifluoromethyl)benzoyl]-2-(1H-indol-3-ylmethyl)-4-{[5-(morpholinomethyl)-2H-1,2,3-triazol-4-yl]methyl}piperazine of Formula I.

The compounds of Formula I and their acid addition salts may be prepared by a) reacting a compound corresponding to formula II:

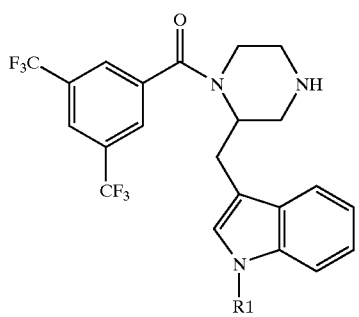

II wherein $R^1$ has the above meaning, with a compound corresponding to formula III:

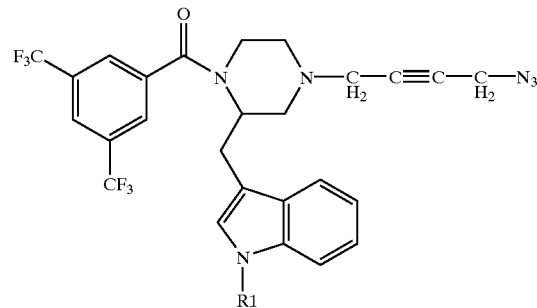

III wherein $R^2$ and $R^3$ have the above meanings, and wherein any reactive groups present are blocked by suitable protective groups, or b) reacting a compound corresponding to formula IV:

IV wherein $R^1$ has the above meaning, with a compound corresponding to formula V:

V

wherein $R^2$ and $R^3$ have the above meanings, and wherein any reactive groups present are blocked by suitable protective groups, and subsequently cleaving off any protective groups which may be present. If desired, a resulting compound of Formula I may be converted into a corresponding acid addition salt, or an acid addition salt may be converted into a free compound of Formula I.

According to process variant a), a secondary amino function of a substituted piperazine derivative of Formula II can be reacted with an N,N-disubstituted azidobutinamine of Formula III to obtain a compound of Formula I. The reaction can be carried out in a solvent which is inert under the reaction conditions, such as a dipolar-aprotic solvent, for example ethyl acetate or dimethyl formamide (=DMF), or preferably in a mixture of such solvents. A mixture of ethyl acetate and DMF is particularly preferred. Suitable reaction temperatures are between room temperature and the boiling temperature of the solvent or of the solvent mixture. Where compounds of Formula III are used which have additional functional groups which are reactive under the reaction conditions, these additional functional groups are expediently blocked by known protective groups. Suitable protective groups, which can be introduced using known methods and later can be cleaved off again using known methods, are known, for example, from J. A. W. McOmie "Protective Groups in Organic Chemistry", Plenum Press 1973, or from T. W. Green and P. G. M. Wuts "Protective Groups in Organic Synthesis", Wiley and Sons 1991. The person skilled in the art can select suitable protective groups for each case by routine methods.

The compounds of Formula II and their stereoisomeric forms are known from EP 0 655 442 A1, and can be prepared according to the processes described in this patent application or analogously to these processes.

Compounds of Formula III can be prepared by reacting a compound of formula VI:

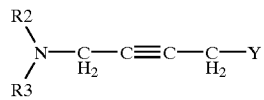

VI wherein $R^2$ and $R^3$ have the above meanings and Y stands for a cleavable leaving group, with an alkali metal azide, preferably sodium azide, in a manner known for azide formation. Suitable leaving groups Y include, in particular, halogen, preferably chlorine, or alternatively sulfonyloxy groups, which form good leaving groups, for example lower-alkane sulfonyloxy such as methanesulfonyloxy, or benzenesulfonyloxy optionally substituted in the benzene ring by halogen or lower alkyl, such as p-toluenesulfonyloxy.

Compounds of Formula VI can be prepared by reacting a compound of Formula V in known manner with a compound corresponding to formula VII:

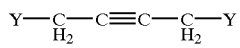

VII wherein Y has the above meaning. Resulting compounds of Formula VI may also be purified if desired. For purification, compounds of Formula VI may for example be converted into suitable salts, such as oxalates, and be purified according to known crystallisation methods. The above salts of the compounds of Formula VI may also be used directly for further reactions.

Secondary amines of Formula V are known per se. The compounds of Formula VII are likewise known per se. Preferably 1,4-dichloro-2-butine can be used as the compound of Formula VII.

According to process variant b), a piperazine-N-butinazide of Formula IV may be reacted with a secondary amine of Formula V to obtain a compound of Formula I. The reaction can be performed in known manner, for example in accordance with a method known from K. Banert, Chemische Berichte 122 (1989) 1963–1967 or by methods analogous thereto, in a solvent which is inert under the reaction conditions such as ethyl acetate or an ether, for example tetrahydrofuran (=THF) or dioxane. If applicable, in a preferred process variant the secondary amine of Formula V itself, for example morpholine, may be used as solvent. A suitable reaction temperature must be selected depending on the secondary amine of Formula V which is used. If the amine of Formula V is liquid or solid at room temperature, usually operation is possible at temperatures between room temperature and the boiling point of conventional solvents, for example up to 100° C. Where readily volatile amines of Formula V are used, for example dimethylamine or diethylamine, it is advantageous to operate at low temperatures, for example between −78° C. and −10° C., and preferably at elevated pressure, for example at 1.5 to 3 bar. Reactions at elevated pressure can be performed in known autoclaves. Where amines of Formula V are used which have additional functional groups which are reactive under the reaction conditions—for example a secondary amino function, if piperazine is used—these additional functional groups are desirably blocked by known protective groups. Suitable protective groups, which can be introduced using known methods and later can be cleaved off again using known methods, are known, for example, from the publications mentioned above in process variant a). Where piperazine is used as the amine of Formula V, the tert. butoxycarbonyl group is preferred as protective group. Persons skilled in the art can select suitable protective groups for each case by routine methods.

Compounds of Formula IV are novel compounds which are suitable as intermediate products for the preparation of novel active substances, for example for the preparation of the compounds of Formula I. The compounds of Formula IV can be prepared by reacting compounds of the formula VIII:

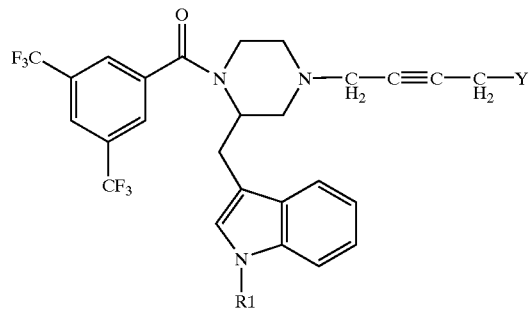

VIII wherein $R^1$ and Y have the above meanings, with an alkali metal azide, preferably sodium azide, in a manner known for azide formation.

Compounds of Formula VIII can be prepared by reacting compounds of Formula II with compounds of Formula VII in known manner.

The compounds of Formula I may be isolated from the reaction mixture and purified in known manner. Acid addition salts can be converted into the free bases in conventional manner, and these may if desired be converted in known manner into physiologically compatible acid addition salts.

Physiologically compatible salts of compounds of Formula I are their salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or benzenesulfonic acids optionally substituted in the benzene ring by halogen or lower alkyl, such as p-toluenesulfonic acid. A preferred salt of a compound of Formula I is (2R)-1-[3,5-bis(trifluoromethyl)benzoyl]-2-(1H-indol-3-ylmethyl)-4-{[5-(morpholinomethyl)-2H-1,2,3-triazol-4-yl]methyl}piperazine-dihydrochloride, since it is comparatively readily soluble in water.

The compounds of Formula I at any rate contain a chiral (asymmetric) carbon atom, namely the carbon atom bearing the 1H-indol-3-ylmethyl radical in position 2 of the piperazine parent structure. The compounds of Formula I can thus exist in several stereoisomeric forms. The present invention comprises both the mixtures of optical isomers and the isomerically pure compounds of Formula I. Preferred are compounds of Formula I in which the indolylmethyl radical is located in position 2R of the piperazine ring. If mixtures of optical isomers of the starting compound, for example the compounds of Formula II or the compounds of Formula IV are used in the synthesis of compounds of Formula I, the compounds of Formula I are also obtained in the form of mixtures of optical isomers. Starting from stereochemically uniform forms of the starting compound, stereochemically uniform compounds of Formula I can also be obtained. The stereochemically uniform compounds of Formula I can be obtained from the mixtures of optical isomers by known techniques, for example by chromatographic separation on chiral separating materials or by reaction with suitable optically active acids, for example tartaric acid or 10-camphorsulfonic acid, and subsequent separation into their optically active antipodes by fractional crystallisation of the resulting diastereomeric salts.

In the compounds of Formula I, the 1,2,3-triazole ring may be present in several tautomeric forms, so the hydrogen atom may be bonded to different atoms of the 1,2,3-triazole ring. Within the scope of the present invention, the compounds of Formula I should jointly comprise all possible tautomers of the triazole ring.

The compounds of Formula I and their acid addition salts have properties which are antagonistic to neurokinin (=NK) receptors and are suitable for the treatment of pathological conditions in larger mammals, particularly humans, in which neurokinins are involved as transfer agents. In this case, the group of compounds according to the invention is distinguished by a particularly beneficial action profile which is characterised by a high selective affinity to NK-1 receptors. Furthermore, the group of compounds according to the invention is distinguished by good compatibility even over prolonged periods of administration, and by comparatively good oral bioavailability.

Due to their activity profile and to their selective and reversible ability to bond to NK-1-receptors, the compounds according to the invention are particularly suitable for inhibiting processes involving neurokinins, such as Substance P, which bind to NK-1 receptors. Thus the compounds are selectively suitable for the treatment of pathological conditions in which Substance P is involved. Substance P plays a part, for example, in the transmission of pain, emesis, neurogenic inflammations, bladder inflammation, inflammatory joint diseases and asthmatic complaints. Owing to the action which is advantageously directed at the peripheral region, the action profile of the compounds is suitable for the treatment of peripheral pathological disturbances, in particular for the treatment of functional and inflammatory disturbances in the gastrointestinal tract. The functional disturbances which can be treated by the compounds according to the invention include in particular the disturbances of the lower intestinal tracts known as so-called "irritable bowel syndrome" (=IBS). The essential symptoms of IBS are pains in the lower abdomen, which appear to be due to hypersensitivity of the visceral afferent nervous system, and anomalies in bowel movement, in particular abnormally accelerated passage of the stool in the colon. The increased visceral sensitivity to pain with respect to mechanical or chemical irritants in the intestinal tract results in IBS patients suffering severe visceral pains even upon only physiological slight distension of the colon owing to digestion, e.g. even upon slight gas formation and slight flatulence, which are scarcely noticed by healthy individuals. Inflammatory disturbances in the gastrointestinal tract which can be favourably influenced by the compounds according to the invention include the inflammatory disturbances in the small intestine and large intestine regions generally grouped under the term IBD (=inflammatory bowel disease), including ulcerative colitis and Crohn's disease. The action profile of the compounds is distinguished by comparatively good oral bioavailability with beneficial selectivity of the actions antagonistic to neurokinin receptors with respect to unwanted side-effects, particularly in therapeutic procedures directed at the peripheral region. Thus, in dose ranges which block the NK-1 receptor, in pharmacological tests no cardiovascular calcium-antagonistic action was detected. Furthermore, it can be assumed of the compounds according to the invention that they have no significant side-effects on the central nervous system.

Description of the Pharmacological Test Methods

The example numbers given for the compounds used as test substances in the pharmacological tests relate to the subsequent preparation examples.

1. Determination of the Binding Power of the Test Substances to NK-1 Receptors in vitro The affinity of the test substances to human NK-1 receptors was measured in vitro. The inhibition of the binding of the physiological neurokinin (Substance P) to neurokinin-1 receptors was determined.

The receptor binding studies were performed with [$^3$H]-Substance P as ligand. For the binding test, different samples of a membrane preparation of CHO cells (=egg cells of the Chinese hamster, Chinese hamster oocytes), which express the human NK-1 receptor ("Accession Number" of the associated nucleic acid sequence=M74290; "Accession Number" of the associated protein sequence=P25103; cf. Takeda, Y.; Chou, K. B., Takeda, J.; Sachais, B. S. and Krause, J. E; Biochemical and Biophysical Research Communications, 179(3) (1991) 1232–1240), were incubated with a solution of the marked ligand, with the incubation mixtures containing no test substance or additions of different concentrations of test substance. Then, separation of bound and free ligands was performed in each of the samples with the aid of glass-fibre filtration. The fraction remaining in the filter was washed several times with buffer solution and then the radioactivity of the fraction remaining in the filter was measured using a beta scintillation counter.

For the compounds of Examples 1 and 8 to 65, the affinity to human NK-1 receptors was determined in each case by a single measurement of the test substances in a concentration of $10^{-7}$ mol/l. All the above test substances in this test model exhibited displacement of the physiological NK-receptor ligand Substance P of $\geq 75\%$. The compounds of Examples 1, 8–15, 17–29, 34–47, 49–55, 57, 59–60 and 62–65 each exhibited a displacement of $\geq 90\%$.

For the compounds of Examples 2 and 4–6, that concentration which effects half maximum displacement of the bound ligand was determined as $IC_{50}$ of the respective test substance. From this, the corresponding inhibition constant ($K_i$ value) of the test substance was calculated, and was stated as the negative common logarithm of the $K_i$ value (=$pK_i$ value). The $pK_i$ value is a measurement of the affinity of the test substances to human NK-1 receptors. In this test model, the test substances set forth in the following Table 1 exhibited the given $pK_i$ values:

TABLE 1

Affinity of the test substances to human NK-1 receptors

| Example No. | pKi |
| --- | --- |
| 2 | 8.4 |
| 4 | 8.3 |
| 5 | 8.3 |
| 6 | 8.4 |

2. Determination of the Functional NK-1 Antagonism of the Test Substances on Isolated Guinea Pig Tissue in vitro The action antagonistic to NK-1 receptors of the test substances was measured in vitro on isolated ring preparations, kept in an oxygenated nutrient solution, of the aortas of Pirbright-White guinea pigs. The inhibition by the test substances of the relaxation of tone of the aorta preparations, caused after stimulation with the NK-1 agonist Substance P, was determined.

In order to measure the contraction of the vessel muscles, the preparations were fixed to a hook, joined by a thread to a force measuring apparatus and the contractions were recorded in each case on a plotter. The aorta preparations were tonicised with phenylephrine. Then before and after the administration of the test substance the NK-1 receptors of the preparations were stimulated with 0.01 μmol Substance P, which caused relaxation of the tone. The relaxations before and after the administration of the test substance were quantified in percent. The effective concentration of the half maximum inhibition of the relaxation of the tone (=$EC_{50}$) was calculated. The negative common logarithm of the $EC_{50}$ value (=$pEC_{50}$) was given as characteristic variable. The $pEC_{50}$ value is a measurement of the functional effectiveness of the test substances on NK-1 receptors. In this test model, the test substances set forth in the following Table 2 exhibited the given $pEC_{50}$ values:

TABLE 2

Functional NK-1 antagonism of the test substances on isolated guinea pig tissue.

| Example No. | $pEC_{50}$ |
|---|---|
| 1 | 9.0 |
| 2 | 9.1 |
| 3 | 8.4 |
| 4 | 8.6 |
| 5 | 8.7 |
| 6 | 8.9 |

3. Determination of the Substance-P-antagonistic Action of the Test Substances in vivo In order to demonstrate the substance-P-antagonistic action of the test substances, the transient hypotension caused by intravenous (=i.v.) administration of Substance P in guinea pigs was used as the standard test model for Substance P-induced pharmacological effects. The inhibiting effect of the test substances was determined with respect to vasodepression induced by Substance P on one hand after i.v. and on the other hand after oral (=p.o.) administration of the test substances.

Male guinea pigs each had a catheter implanted in a common carotid artery and a jugular vein under anaesthesia (ketamine 67 mg/kg, xylazine 13 mg/kg). The arterial catheter served to measure the blood pressure. The administration of Substance P and, in the case of i.v. administration, also the administration of the test substance, was effected by means of the venous access. After a 20-minute equilibration phase, 50 pmol/animal of Substance P were administered (bolus, i.v.) as a test stimulus. One minute after administration of the test stimulus, in each case the maximum drop in blood pressure induced thereby was determined as a control for the later stimulation of the NK-1 receptors by the test substance. Then the test substance was administered. For the i.v. investigation, the test substance was administered in metered doses of 0.01 to 0.1 μmol/kg. For the p.o. investigation, the test substance was administered in metered doses of 0.1 to 3.2 μmol/kg. Tylose or Tylose/ethanol was used as the vehicle for the p.o. investigations. Then, in each case the extent of the vasodepression inhibited by the test substance was measured, starting 1 minute after administration of test substance, up to 90 minutes after administration of test substance, at intervals of 15 minutes each time. The doses at which, dependent on the time, just 50% inhibition of the Substance P-induced vasodepression occurs due to the test substance were determined from these measured values as $ED_{50}$ values. The negative common logarithm of the $ED_{50}$ value (=$pED_{50}$) was given as characteristic variable.

In this test model, the test substance of Example 1 exhibited a $pED_{50}$ value of 7.6 one hour after i.v. administration. The same test substance of Example 1 showed a $pED_{50}$ value of 6.2 one hour after p.o. administration. The compound of Example 6 showed a $pED_{50}$ value of 7.0 one hour after i.v. administration. These values prove the high pharmacological potency of the compounds of Formula I, in particular also for oral administration.

In the same test model, the test substances were also investigated for vasodepressive effects based on calcium-antagonistic properties. To this end, the action of the test substances on the basal blood pressure was investigated. The substance of Example 1 exhibited no significant vasodepression in the dose range investigated (i.v. doses of up to 0.1 μmol/kg and p.o. doses of up to 3.2 μmol/kg). This is an indication that no calcium-antagonistic side-effects occurred in this dose range. The low calcium-antagonistic side-effects of the compounds according to the invention can also be demonstrated by in vitro standard test models, for example on isolated ileum tissue of guinea pigs.

In a standard test to determine CNS-permeable compounds having an NK-1-antagonistic effect ("gerbil foot tapping test", cf. N. M. Rupniak, A. R. Williams, European Journal of Pharmacology 265 (1994) 179–183), the compound of Example 1 did not exhibit any typical effects of CNS-permeable NK-1 antagonists even at high doses of up to 30 mg/kg p. o.

The compounds of Formula I may be administered in conventional pharmaceutical preparations. The doses to be used may vary individually and will naturally vary according to the type of condition to be treated and the substance used. In general, however, medicinal forms with an active substance content of 0.1 to 80 mg, in particular 1 to 10 mg, active substance per individual dose are suitable for administration to humans and larger mammals.

The compounds may be contained according to the invention, together with conventional pharmaceutical auxiliaries and/or carriers, in solid or liquid pharmaceutical preparations. Examples of solid preparations are preparations which can be administered orally, such as tablets, coated tablets, capsules, powders or granules, or alternatively suppositories. These preparations may contain conventional pharmaceutical inorganic and/or organic carriers, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or carriers in known manner. For the production of solid medicament forms, the active substances may for example be mixed with the auxiliaries and/or carriers in conventional manner and may be wet or dry granulated. The granules or powder can be poured directly into capsules or be pressed into tablet cores

13 in conventional manner. These can be coated in known manner if desired.

The following examples are intended to illustrate the invention in further detail, without limiting its scope.

EXAMPLE 1

(2R)-1-[3,5-Bis(trifluoromethyl)benzoyl]-2-(1H-indol-3-ylmethyl)-4-{[5-(morpholinomethyl)-2H-1,2,3-triazol-4-yl]methyl}piperazine Synthesis method 1

A) 22 ml 1,4-dichloro-2-butine was added to a suspension of 43 g $K_2CO_3$ in 100 ml DMF at 20° C. under a protective gas atmosphere. The mixture was heated to 50° C. and then a solution of 50 g (2R)-1-[3,5-bis(trifluoromethyl)-benzoyl]-2-(1H-indol-3-ylmethyl)piperazine in 200 ml DMF was added dropwise to this receiving solution. The resulting mixture was stirred for 5 hours at 50° C. Stirring was continued overnight at room temperature, undissolved precipitate was filtered out, and the precipitate was washed twice with 200 ml portions of ethyl acetate. The combined filtrates were evaporated to dryness in a vacuum, and the resulting oil was purified by column chromatography (silica gel; mobile solvent: n-hexane/ethyl acetate 60/40 to 30/70). The combined product fractions were again evaporated to dryness. 40.4 g of (2R)-1-[3,5-bis(trifluoromethyl)-benzoyl]2-(1H-indol-3-ylmethyl)-4-(4-chloro-2-butin-1-yl)piperazine was obtained as an amorphous yellowish solid, which was used for the next synthesis stage without further purification.

B) 5.76 g $NaN_3$ were added to a solution of 40.0 g of the chlorobutinyl-piperazine derivative obtained above under 1A) in 200 ml dimethyl sulfoxide (=DMSO) at room temperature and under a protective gas atmosphere. The resulting mixture was stirred further for 24 hours under a protective gas atmosphere at room temperature. A solution of 50 g ammonium chloride in 300 ml water was added to this receiving solution. Then the aqueous phase was extracted with 500 ml methyl-tert. butyl ether (=MTBE). The organic phase was washed in succession with 200 ml saturated common salt solution and 200 ml water, dried over sodium sulfate and finally evaporated to dryness in a vacuum. The remaining yellowish foam was purified by column chromatography (silica gel; mobile solvent: ethyl acetate/n-hexane 65/35 to 80/20). The combined product fractions were again evaporated to dryness. 33.2 g (2R)-1-[3,5-bis(trifluoromethyl)benzoyl]2-(1H-indol-3-ylmethyl]-4-(4-azido-2-butin-1-yl)piperazine were obtained as a yellowish solid, which was used for the next synthesis stage without further purification.

C) 25.5 g of the azido derivative obtained above under 1B) were dissolved in 10 ml morpholine and were heated to 80° C. for 4 hours under a protective gas atmosphere. The reaction mixture was stirred further overnight at room temperature and was then evaporated to dryness in a vacuum. The residue was taken up in 500 ml ethyl acetate and again evaporated to dryness in a vacuum. The resulting foam was purified by column chromatography (silica gel; mobile solvent: ethyl acetate/ethanol 100/0 to 85/15). The combined product fractions were evaporated to dryness. 22.0 g of the title compound were obtained as a yellowish amorphous solid, melting point=92° to 98° C. (glass transition temperature), $[\alpha]_D^{20}$=5° (c=1.0 in methanol).

D) 20 ml absolute ethanol were added to a solution of 39.0 g of the title compound obtained above under 1C) in 100 ml MTBE under a protective gas atmosphere. The resulting reaction mixture was heated to 40° to 50° C. and 81 ml of a 1.6 N HCl in isopropanol was added to this receiving solution. The reaction mixture was stirred for another 10 minutes at 50° C. Then 1,000 ml MTBE were added slowly, whereupon the salt began to precipitate. Stirring was continued for 2 hours at room temperature to complete the precipitation, the precipitate was filtered out from the liquid phase and the salt was washed twice with MTBE. After drying in a vacuum, 39.5 g of the solid title compound was obtained as a white to beige dihydrochloride, melting point. =213° to 216° C.; $[\alpha]_D^{20}$=−3.6° (c=1.0 in methanol).

Synthesis Method 2

A) 17.0 ml of 1,4-dichloro-2-butine were dissolved in 100 ml toluene under a protective gas atmosphere, and 42.6 g $K_2CO_3$ were added to the solution. Once the resulting suspension had been heated to 50° C., a solution of 10 ml morpholine in 100 ml toluene was slowly added dropwise to this receiving solution. The resulting reaction mixture was stirred for another 5 hours at 50° C. and then overnight at room temperature. The $K_2CO_3$ was filtered out, subsequently washed twice with 100 ml toluene each time and the combined filtrates were reduced in a vacuum. The residue was taken up with about 100 ml toluene and the organic phase was washed in succession with saturated aqueous solutions of $NaHCO_3$ and NaCl. The organic phase was evaporated to dryness in a vacuum. 14.3 g crude 1-(4-chloro-2-butin-1-yl)morpholine was obtained as an oil, which was converted into the monooxalate for purification.

For purification, 14.0 g of the crude compound obtained above were taken up in 80 ml MTBE. The precipitate was filtered out and subsequently washed twice with 100 ml portions of MTBE. The combined filtrates were heated to 50° C. under a protective gas atmosphere. A solution at 50° C. of 10.0 g oxalic acid in 40 ml ethanol was added to this receiving solution. After cooling to room temperature, the reaction mixture was stirred overnight. The resulting oxalate was filtered out, and the solid was subsequently washed three more times with 20 ml portions of MTBE. 13.0 g [1-(4-chloro-2-butin-1-yl)morpholine]-monooxalate were obtained, melting point=144–146° C.

B) 510 g of the oxalic acid salt obtained above under Example 1/Synthesis method 2A) were dissolved in 10 ml DMF at room temperature under a protective gas atmosphere. 154 mg $NaN_3$ were added to this receiving solution, and the solution was stirred for 10 minutes. Then 0.6 ml triethylamine was added. The resulting suspension was stirred further for another 15 hours, and the resulting 1-(4-azido-2-butin-1-yl)morpholine was used directly in the suspension without further working-up or characterization for the next synthesis stage.

C) The suspension of the azido compound obtained above under Example 1/Synthesis method 2B) was diluted with 60 ml ethyl acetate. 1.5 ml of a 55% by weight solution of (2R) -1-[3,5-bis (trifluoromethyl)benzoyl]-2-(1H-indol-3-ylmethyl)piperazine in THF were added to this receiving solution, and the resulting mixture was heated to boiling point for 15 hours and was then stirred further for another 3 days at room temperature. The resulting solution was washed 3 times with 50 ml portions of water, and the organic phase was dried over sodium sulfate. The residue remaining after evaporation and drying in a high vacuum was identified as the title compound by combined liquid chromatography/mass spectroscopy (=LC/MS).

EXAMPLE 2

(2R)-1-[3,5-Bis(trifluoromethyl)benzoyl]-2-(1H-indol-3-ylmethyl)-4-{[5-(piperazinomethyl)-2H-1,2,3-triazol-4-yl)]methyl}piperazine A) 1.0 g (2R) -1-[3,5-bis (trifluoromethyl) benzoyl]-2-(1H-indol-3-ylmethyl)-4-[4-azido-2-butin-1-yl]piperazine (for preparation see Example 1/Synthesis method 1B)) was dissolved in 50 ml ethyl acetate under a protective gas atmosphere. 0.4 g tert. butoxycarbonylpiperazine was added to this receiving solution, and the resulting reaction mixture was heated for 8 hours to 80° C. under reflux cooling. Stirring was effected overnight at room temperature, and the organic phase was then washed three times with 10 ml portions of water. The organic phase was dried over sodium sulfate and evaporated to dryness in a vacuum. 1.4 9 (2R)-1-[3,5-bis(trifluoromethyl)benzoyl]-2-(1-methyl-indol-3-ylmethyl)-4-{[5-(4-tert. butoxycarbonylpiperazin-1-yl)-2H-1,2,3-triazol-4-yl]methyl}piperazine was obtained as a yellowy-brown foam, which was used directly for the next synthesis stage without further purification.

B) 330 mg of the compound obtained above under 2A) was dissolved in 10 ml methanol. 10 ml of a 1.5 N HCl solution in isopropanol was added to this receiving solution, and the resulting reaction mixture was stirred overnight at room temperature. A solution of 0.4 g NaOH in 10 ml water was then added to this receiving solution. Evaporation virtually to dryness was effected in a vacuum, and the residue was extracted with 50 ml $CH_2Cl_2$. The organic phase was washed with 100 ml water and evaporated to dryness in a vacuum. 270 mg of a hydrochloric acid salt of the title compound were obtained as a foam, melting point >200° C.

EXAMPLE 3

(2R)-1-[3,5-bis(trifluoromethyl)benzoyl]-2-(1-methyl-indol-3-methyl)-4-{[5-(morpholinomethyl)-2H-1,2,3-triazol-4-yl)]methyl}piperazine A) First 50 ml of a 55% by weight solution of (2R)-1-[3,5-bis(trifluoromethyl)benzoyl]-2-(1H-indol-3-ylmethyl)-piperazine in THF and then 25 ml water were added to a suspension of 7.4 9 $K_2CO_3$ in 150 ml THF. A solution of 12.2 g tert. butoxycarbonyl anhydride in 50 ml THF was added to this receiving solution, and the mixture was stirred for 12 hours at room temperature. After reduction of the reaction mixture in a vacuum, the residue was taken up in 300 ml MTBE, and the organic phase was washed, in succession, twice with 100 ml portions of water, once with 50 ml of a 15% by weight aqueous tartaric acid solution and another four times with 100 ml portions of water, and then dried over sodium sulfate/$SiO_2$. After filtering out the drying agent, the filtrate was reduced in a vacuum, and the residue was taken up in 20 ml MTBE. After heating to 60° C., 120 ml ligroin was added, and the volume was then reduced by approximately 100 ml by vacuum distillation. After another addition of 100 ml ligroin, the mixture was left to stand for 3 days to precipitate. The precipitated solid was filtered out, washed three times more with 30 ml portions of ligroin and dried at 60° C. in a vacuum. 82.0 g of (2R)-1-[3,5-bis(trifluoromethyl)benzoyl]-2-(1H-indol-3-ylmethyl]-4-(tert.butoxycarbonyl)piperazine were obtained as a solid, melting point 155–156° C.

B) 5.0 g of the BOC-protected piperazine derivative obtained above under 3A) were dissolved in 100 ml dry DMF at room temperature under a protective gas atmosphere. 0.2 g NaH (60% strength in mineral oil) was added to this receiving solution and the solution was stirred further for 10 minutes. Then a solution of 1.9 ml $CH_3I$ in 5 ml DMF was added dropwise, and stirring was continued for 4 hours at room temperature once addition had been completed. The reaction mixture was poured on to a mixture of 100 g ice, 18 g $Na_2S_2O_3$ and 50 ml water. The aqueous phase was extracted with a mixture of 200 ml ethyl acetate and 100 ml MTBE. The organic phase was washed once with water and was evaporated to dryness in a vacuum. The oily residue was taken up in 100 ml methanol, washed with 50 ml diethyl-ether and again evaporated to dryness. 5.5 g (2R)-1-[3,5-bis(trifluoromethyl)benzoyl]-2-(1-methyl-indol-3-ylmethyl)-4-(tert.butoxycarbonyl)piperazine was obtained as a glassy solid, which was used directly for the next synthesis stage without purification or characterization.

C) 5.9 g of the indolyl-N-methylated piperazine derivative obtained above under 3B) were dissolved in 60 ml methanol. A total of 10 ml of an aqueous 1N HCl solution was added slowly to this receiving solution and was stirred for 48 hours at room temperature. The reaction mixture was taken up in 100 ml methanol and washed twice with 20 ml portions of n-hexane. The methanol phase was reduced in a vacuum, and the residue was taken up in a mixture of 100 ml water and 100 ml MTBE and left to stand overnight. Then the organic phase was decanted off as supernatant from the aqueous phase and extracted 3 times with 30 ml portions of 0.1 N aqueous HCl. The organic phase was neutralized with a saturated aqueous solution of $K_2CO_3$, whereupon a first fraction (2R)-1-[3,5-bis(trifluoromethyl)benzoyl]-2-(1-methyl-indol-3-ylmethyl)piperazine was produced as an amorphous solid, which was purified by conversion into the oxalate and subsequent neutralization back to the base. A further solid fraction was obtained by neutralizing the aqueous phase. The combined solid fractions, which were obtained by filtration from the organic and the aqueous phase, were dried in a high vacuum. A total of 4.6 g of the above de-protected indolyl-N-methylated piperazine derivative was obtained.

D) 0.52 ml 1,4-dichloro-2-butine was reacted with 1.2 g of the de-protected indolyl-N-methylated piperazine derivative obtained above under 3C) as described under Example 1/Synthesis method 1A). After chromatography (silica gel, mobile solvent: ethyl acetate/n-hexane 65/35 to 80/20), 840 mg (2R)-1-[3,5-bis(trifluoromethyl)-benzoyl]-2-( 1-methyl-indol-3-ylmethyl]-4-(4-chlor-2-butin-1-yl) was obtained as a foam, which was used for the next synthesis stage without further purification.

E) 820 mg of the chlorobutinyl-piperazine derivative obtained above under 3D) were reacted with 130 mg $NaN_3$ as described under Example 1/Synthesis method 1B). 760 mg (2R)-1-[3,5-bis(trifluoromethyl)benzoyl]-2-[1-methyl-indol-3-ylmethyl]-4-[4-azido-2-butin-1-yl]piperazine were obtained as a foam, which was used for the next synthesis stage without further purification.

F) 740 mg of the azido compound obtained above under 3E) were dissolved in 15 ml of morpholine. The reaction mixture was worked up as described under Example 1/Synthesis method 1C). After chromatography (silica gel, mobile solvent: $CH_2Cl_2$/ethanol), 470 mg of the title compound were obtained as a white solid, which was used for the next synthesis stage without further purification.

G) 440 mg of the title compound obtained above under 3F) were converted into the HCl salt with 1 ml of a 1.6 N HCl solution in isopropanol as described under Example 1/Synthesis method 1D). 425 mg of the dihydrochloride monohydrate of the title compound were obtained as a solid, melting point=192°–200° C.

EXAMPLE 4

(2R)-1-[3,5-Bis(trifluoromethyl)benzoyl]-2-(1H-indol-3-ylmethyl)-4-{[5-(dimethylaminomethyl)-2H-1,2,3-triazol-4-yl]methyl}piperazine 660 mg (2R)-1-[3,5-bis(trifluoromethyl)benzoyl]-2-(1H-indol-3-ylmethyl)-4-[4-azido-2-butin-1-yl]piperazine (for preparation see Example 1/Synthesis method 1B)) were poured into an autoclave precooled to −20° C. To this there was added a solution, cooled to −20° C., of 2 moles dimethylamine in 30 ml THF. Once the autoclave had been closed, the mixture was stirred for one day at 70° C. and at a pressure of 2.0 to 2.2 bar. Then stirring was continued overnight at room temperature under conditions which were otherwise unchanged. The reaction mixture was evaporated to dryness in a vacuum, and 700 mg of the title compound were obtained as foam.

For salt formation, 680 mg of the title compound were dissolved in 10 ml methanol. 1.5 ml of a 1.5N HCl solution in isopropanol were added to this receiving solution, and it was then evaporated to dryness under a high vacuum. The residue was taken up twice in 20 ml portions of methanol and each time evaporated again to dryness. The remaining residue was suspended in 10 ml MTBE and heated to boiling point for 2 hours with reflux cooling. After cooling to room temperature and subsequent filtration, the solid precipitate was washed three times with 10 ml portions of MTBE and dried under a high vacuum. 670 mg of a dihydrochloride dihydrate salt of the title compound were obtained as an amorphous solid, which was characterized, inter alia, by elemental analysis.

The compounds of Formula I set forth in the following Table 3 can also be prepared according to the processes described in the, above examples or by processes analogous thereto. Whenever in Tables 3 and 4 below the substituents $R^2$ and $R^3$ together stand for "a", $R^2$ and $R^3$, together with the nitrogen to which they are bonded, form a cyclic group of formula a as described above in which $R^4$, $R^5$, A and n each have the meanings set forth in the tables.

TABLE 3

Further compounds of formula I

| Ex. No. | Configuration at the indolyl-piperazine C - 2 | $R^1$ | $R^2$ | $R^3$ | $R^4$ | $R^5$ | A | n |
|---|---|---|---|---|---|---|---|---|
| 5 | R | H | Et | Et | — | — | — | — |
| 6 | R | H | i-Pr | i-Pr | — | — | — | — |
| 7 | S | H | a | | H | H | O | 2 |

Abbreviations used: i-Pr=isopropyl; Et=ethyl

The following compounds of Examples 8 to 65 were prepared using an automated preparation process. For this, per batch a solution of 0.03 mmol (2R)-1-[3,5-bis(trifluoromethyl)benzoyl]-2-(1H-indol-3-ylmethyl) -4-(4-azido-2-butin-1-yl)piperazine of Formula IV (for preparation see Example 1/Synthesis method 1B)) in 1 ml ethyl acetate was reacted each time with a solution of 0.03 mmol of the secondary amine of Formula V provided as reaction participant in 1 ml ethyl acetate and then diluted with 3 ml ethyl acetate. Nitrogen gas was poured on to the reaction mixtures and they were each stirred for 6 hours at 70° C. The end point of the reaction was determined by thin-layer chromatography. Once the reaction was completed, the individual reaction mixtures were each evaporated to dryness in a vacuum. Samples were each taken from the residue without further purification for high-performance liquid chromatography (=HPLC) and for automatic mass spectroscopy to determine the purity and to confirm the structure.

The compounds of Formula I set forth in the following Table 4 can be prepared using the automated preparation process referred to above. All the compounds of Formula I listed in Table 4 have the R configuration at the carbon C-2 of the piperazine structure which bears the indolylmethyl radical.

TABLE 4

Further compounds of the general formula I

| Ex. No. | $R^1$ | $R^2$ | $R^3$ | $R^4$ | $R^5$ | A | n |
|---|---|---|---|---|---|---|---|
| 8  | H | c-$C_6H_{11}$ | Me | — | — | — | — |
| 9  | H | a | | H | H | HC= | 1 |
| 10 | H | a | | 2-Me | 5-Me | $CH_2$ | 1 |
| 11 | H | a | | 4-Me | H | $N(R^4)$ | 2 |
| 12 | H | a | | 4-Bzl | H | $N(R^4)$ | 2 |
| 13 | H | a | | 3-Me | 5-Me | O | 2 |
| 14 | H | a | | 4-(—O—$(CH_2)_2$—O—)-4 | | $CR^4R^5$ | 2 |
| 15 | H | a | | H | H | $CH_2$ | 2 |
| 16 | H | a | | 3-COOEt | H | $CH_2$ | 2 |
| 17 | H | a | | 4-(pyridyl-2) | H | $N(R^4)$ | 2 |
| 18 | H | —$(CH_2)_2$—(pyridyl-2) | Me | — | — | — | — |
| 19 | H | a | | 4-(piperidinyl-1) | H | $CHR^4$ | 2 |
| 20 | H | (1-Me—piperidinyl-4) | Me | — | — | — | — |
| 21 | H | —$(CH_2)_2$—$NMe_2$ | Me | — | — | — | — |
| 22 | H | —$(CH_2)_3$—$NMe_2$ | Me | — | — | — | — |
| 23 | H | a | | 2-(pyridyl-3) | H | $CH_2$ | 1 |
| 24 | H | —$CH_2$—(pyridyl-3) | Me | — | — | — | — |
| 25 | H | —$CH_2$—(pyridyl-4) | Et | — | — | — | — |
| 26 | H | i-Pr | t-Bu | — | — | — | — |
| 27 | H | a | | (2S)—COOt—Bu | H | $CH_2$ | 1 |
| 28 | H | a | | 4-(pyrralidinyl-1) | H | $CHR^4$ | 2 |
| 29 | H | a | | 2-$(CH_2)_4$-3 | | $CH_2$ | 2 |
| 30 | H | a | | 2-(=CH—CH=CH—CH=)-3 | | =C= | 2 |
| 31 | H | Bzl | i-Pr | — | — | — | — |
| 32 | H | i-Bu | i-Bu | — | — | — | — |
| 33 | H | c-$C_6H_{11}$ | c-$C_6H_{11}$ | — | — | — | — |
| 34 | H | a | | (2S)—$CH_2$—(pyrralidinyl-1) | H | $CH_2$ | 1 |

TABLE 4-continued

Further compounds of the general formula I

| Ex. No. | R¹ | R² | R³ | R⁴ | R⁵ | A | n |
|---|---|---|---|---|---|---|---|
| 35 | H | a | | 4-CH(CH₃)—Phe | H | N(R⁴) | 2 |
| 36 | H | a | | 4-CH₂—C(O)OEt | H | N(R⁴) | 2 |
| 37 | H | a | | 4-(CH₂)₂—Phe | H | N(R⁴) | 2 |
| 38 | H | a | | 4-(pyrimidyl-2) | H | N(R⁴) | 2 |
| 39 | H | a | | 4-(pyrazolyl-2) | H | N(R⁴) | 2 |
| 40 | H | —CH₂—C(O)OEt | —CH₂—C(O)OEt | — | — | — | — |
| 41 | H | t-Bu | Me | — | — | — | — |
| 42 | H | a | | 4-c-C₆H₁₁ | H | N(R⁴) | 2 |
| 43 | H | a | | 4-Me | H | N(R⁴) | 3 |
| 44 | H | —(CH₂)₂—[3,4-bi(OMe)—Phe] | Me | — | — | — | — |
| 45 | H | a | | 4-i-Pr | H | N(R⁴) | 2 |
| 46 | H | a | | 4-(CH₂)₂—(morpholinyl-1) | H | N(R⁴) | 2 |
| 47 | H | a | | (2R)—CH₂Ome | (5R)—CH₂OMe | CH₂ | 1 |
| 48 | H | —CH₂—(furonyl-2) | z-(CH₂)₂C(O)OEt | — | — | — | — |
| 49 | H | a | | 4-[(2-OMe—)Phe] | H | CHR⁴ | 1 |
| 50 | H | a | | 4-Bzl | H | N(R⁴) | 3 |
| 51 | H | a | | 4-(4-F—Bzl) | H | N(R⁴) | 2 |
| 52 | H | a | | 4-CH₂—c-C₆H₁₁ | H | N(R⁴) | 2 |
| 53 | H | a | | 4-Phe | H | CHR⁴ | 2 |
| 54 | H | 2-(CH₂)₂—Phe | Me | — | — | — | — |
| 55 | H | a | | 2-Me | H | CH₂ | 1 |
| 56 | H | —(CH₂)₂—O—(4-Cl—Phe) | Me | — | — | — | — |
| 57 | H | c-C₅H₉ | Me | — | — | — | — |
| 58 | H | dodecahydro-1H-carbazolyl-1- | Me | — | — | — | — |
| 59 | H | —CH₂—(3-Me—pyridyl-2) | Me | — | — | — | — |
| 60 | H | a | | 2-CH₂—NEt₂ | H | CH₂ | 2 |
| 61 | H | a | | 3-Phe | 3-Me | CH₂ | 2 |
| 62 | H | a | | 4-(6-Me—pyridyl-2) | H | N(R²) | 2 |
| 63 | H | a | | 4-CH₂—(Pyridyl-4) | H | N(R²) | 2 |
| 64 | H | a | | 4-(CH₂)₃—(pyrrolidinyl-1) | H | N(R²) | 2 |
| 65 | H | a | | 4-(3-Me—Bzl) | H | N(R²) | 2 |

Abbreviations used:
c = cyclo;
Me = methyl;
Et = ethyl
Phe = phenyl;
Bzl = benzyl;
i-Pr = isopropyl;
i-Bu = isobutyl;
t-Bu = tert. butyl.

EXAMPLE I

Capsules Containing (2R)-1-[3,5-bis(trifluoromethyl)benzoyl]-2-(1H-indol-3-ylmethyl)-4-[(-5-(morpholino-methyl)-2H-1,2,3-triazol-4-yl)methyl]piperazine Capsules with the following composition per capsule were produced:

| | |
|---|---|
| (2R)-1-[3,5-bis(trifluoromethyl)benzoyl]-2-(1H-indol-3-ylmethyl)-4-[(5-(morpholinomethyl)-2H-1,2,3-triazol-4-yl)methyl]piperazine | 20 mg |
| Corn starch | 60 mg |
| Lactose | 300 mg |
| Ethyl acetate | q.s. |

The active substance, the corn starch and the lactose were processed into a homogenous pasty mixture using ethyl acetate. The paste was ground and the resulting granules were placed on a suitable tray and dried at 45° C. in order to remove the solvent. The dried granules were passed through a crusher and mixed in a mixer with the following auxiliaries:

| | |
|---|---|
| Talcum | 5 mg |
| Magnesium stearate | 5 mg |
| Corn starch | 9 mg | and then poured into 400 mg capsules (=capsule size 0).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I:

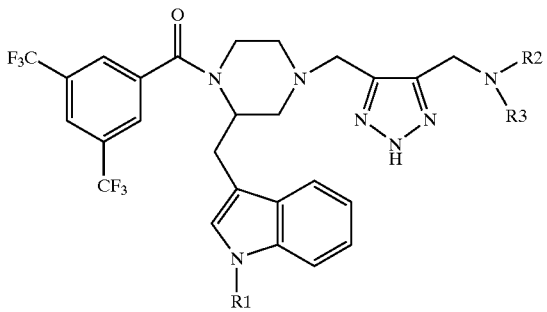

wherein

R¹ is hydrogen or lower alkyl,

R² is lower alkyl, di-lower-alkylamino lower alkyl, lower-alkoxycarbonyl lower alkyl; cyclo(hetero)alkyl having 5–6 ring atoms, which may optionally be substituted once or twice by lower alkyl and which optionally contains 1–2 double bonds; (hetero)phenyl lower alkyl optionally substituted once or twice in the (hetero)phenyl ring by halogen, lower alkyl and/or lower alkoxy, the lower-alkyl chain of which (hetero)phenyl lower alkyl is optionally substituted once or twice by lower alkyl or by spiro-C₄–C₅-alkylene; or phenyl lower alkoxy optionally substituted once or twice in the phenyl ring by halogen, lower alkyl and/or lower alkoxy, and R³ is lower alkyl, lower-alkoxycarbonyl lower alkyl or cyclo(hetero)alkyl with 5–6 ring atoms which is optionally substituted once or twice by lower alkyl, or R² and R³, together with the nitrogen to which they are bonded, form a cyclic group of formula a:

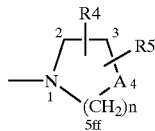

wherein

A is nitrogen, oxygen, methylene or methylidene, the double bond of which, together with the adjacent carbon, is formed in position 3 of group a, n is a whole number from 1 to 3, R⁴ is hydrogen, lower alkyl, lower-alkoxy lower alkyl, lower alkoxycarbonyl, lower-alkoxycarbonyl lower alkyl, di-lower-alkylamino lower alkyl; (hetero)phenyl optionally substituted once or twice by halogen, lower alkyl and/or lower alkoxy; (hetero)phenyl lower alkyl optionally substituted once or twice in the (hetero)phenyl ring by halogen, lower alkyl and/or lower alkoxy, the lower-alkyl chain of which (hetero)phenyl lower alkyl is optionally substituted once or twice by lower alkyl; cyclo(hetero)alkyl with 5–6 ring atoms, or cyclo(hetero)alkyl lower alkyl, the cyclo(hetero)alkyl group of which has 5–6 ring atoms, and R⁵ is hydrogen, lower alkyl or lower-alkoxy lower alkyl, or R⁴ and R⁵ together are spiroethylenedioxy bonded to a carbon of group a; C₃–C₄-alkylene bonded to two adjacent atoms of group a; or phenyl fused via two adjacent carbons of group a, or R² and R³, together with the nitrogen to which they are bonded, form a pyrrolidine ring which is substituted twice by C₄-alkylene which is bonded each time via two adjacent carbon atoms, or a physiologically compatible acid addition salts thereof.

2. A compound according to claim 1, wherein:

R¹ is hydrogen,

R² is lower alkyl, di-lower-alkylamino lower alkyl, lower-alkoxycarbonyl lower alkyl; cyclo(hetero)alkyl with 5–6 ring atoms, optionally substituted once by lower alkyl; heterophenyl lower alkyl optionally substituted once or twice in the heterophenyl ring by lower alkyl or lower alkoxy, or phenyl-C₂–C₄-alkyl substituted once or twice in the phenyl ring by lower alkyl or lower alkoxy, and R³ is lower alkyl or lower-alkoxycarbonyl lower alkyl, with the proviso that R² and R³ do not simultaneously stand for isobutyl, or R² and R³, together with the nitrogen to which they are bonded, form a cyclic group of formula a, wherein n is a whole number from 1 to 3, with the proviso that n stands for 2 or 3, provided that R⁴ and R⁵ are both hydrogen and at the same time A stands for methylene, R⁴ is hydrogen, lower alkyl, lower-alkoxy lower alkyl, lower-alkoxycarbonyl lower alkyl, di-lower-alkylamino lower alkyl; (hetero)phenyl optionally substituted once by lower alkyl or lower alkoxy; (hetero)phenyl lower alkyl optionally substituted once in the (hetero)phenyl ring by halogen, lower alkyl or lower alkoxy; cyclo(hetero)alkyl with 5–6 ring atoms, or cyclo(hetero)alkyl lower alkyl, the cyclo(hetero)alkyl radical of which has 5–6 ring atoms, and R⁵ is hydrogen, lower alkyl or lower alkoxy lower alkyl, with the proviso that R⁴ and R⁵ are not bonded to the same ring atom of group a, or R⁴ and R⁵ together are spiroethylenedioxy bonded to a carbon of group a; or C₃–C₄-alkylene bonded to two adjacent ring atoms of group a.

3. A compound according to claim 1, wherein the carbon C-2 of the piperazine ring which bears the 1H-indol-3-yl-methyl radical is in the R configuration.

4. A compound according to claim 1, comprising group a which represents pyrrolidine substituted by R⁴ and R⁵, wherein R⁴ and R⁵ are not both simultaneously hydrogen, or a represents 2,5-dihydropyrrole, piperidine, piperazine, morpholine or diazepan, each substituted by R⁴ and R⁵.

5. (2R)-1-[3,5-Bis(trifluoromethyl)benzoyl]-2-(1H-indol-3-ylmethyl)-4-{[5-(morpholinomethyl)-2H-1,2,3-triazol-4-yl]methyl}piperazine according to claim 4.

6. (2R)-1-[3,5-Bis(trifluoromethyl)benzoyl]-2-(1H-indol-3-ylmethyl)-4-{[5-(morpholinomethyl)-2H-1,2,3-triazol-4-yl]methyl}piperazine dihydrochloride according to claim 4.

7. A pharmaceutical composition comprising a pharmacologically active amount of a compound according to claim 1 and at least one pharmaceutical carrier or adjuvant.

8. A process for preparing a compound corresponding to formula I:

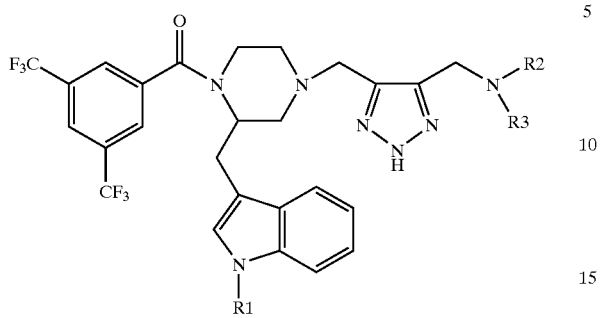

wherein
R¹ is hydrogen or lower alkyl,
R² is lower alkyl, di-lower-alkylamino lower alkyl, lower-alkoxycarbonyl lower alkyl; cyclo(hetero)alkyl having 5–6 ring atoms, which may optionally be substituted once or twice by lower alkyl and which optionally contains 1–2 double bonds; (hetero)phenyl lower alkyl optionally substituted once or twice in the (hetero) phenyl ring by halogen, lower alkyl and/or lower alkoxy, the lower-alkyl chain of which (hetero)phenyl lower alkyl is optionally substituted once or twice by lower alkyl or by spiro-$C_4$–$C_5$-alkylene; or phenyl lower alkoxy optionally substituted once or twice in the phenyl ring by halogen, lower alkyl and/or lower alkoxy, and
R³ is lower alkyl, lower-alkoxycarbonyl lower alkyl or cyclo(hetero)alkyl with 5–6 ring atoms which is optionally substituted once or twice by lower alkyl, or
R² and R³, together with the nitrogen to which they are bonded, form a cyclic group of formula a,

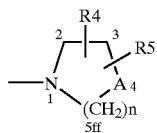

wherein
A is nitrogen, oxygen, methylene or methylidene, the double bond of which, together with the adjacent carbon, is formed in position 3 of group a,
n is a whole number from 1 to 3,
R⁴ is hydrogen, lower alkyl, lower-alkoxy lower alkyl, lower alkoxycarbonyl, lower-alkoxycarbonyl lower alkyl, di-lower-alkylamino lower alkyl, (hetero) phenyl optionally substituted once or twice by halogen, lower alkyl and/or lower alkoxy; (hetero) phenyl lower alkyl optionally substituted once or twice in the (hetero)phenyl ring by halogen, lower alkyl and/or lower alkoxy, the lower-alkyl chain of which (hetero)phenyl lower alkyl is optionally substituted once or twice by lower alkyl; cyclo(hetero) alkyl with 5–6 ring atoms, or cyclo(hetero)alkyl lower alkyl, the cyclo(hetero)alkyl group of which has 5–6 ring atoms, and
R⁵ is hydrogen, lower alkyl or lower-alkoxy lower alkyl, or
R⁴ and R⁵ together are spiroethylenedioxy bonded to a carbon of group a; $C_3$–$C_4$-alkylene bonded to two adjacent atoms of group a; or phenyl fused via two adjacent carbons of group a, or R² and R³, together with the nitrogen to which they are bonded, form a pyrrolidine ring which is substituted twice by $C_4$-alkylene which is bonded each time via two adjacent carbon atoms,
or a physiologically compatible acid addition salt thereof, said process comprising:
a) reacting a compound corresponding to formula II:

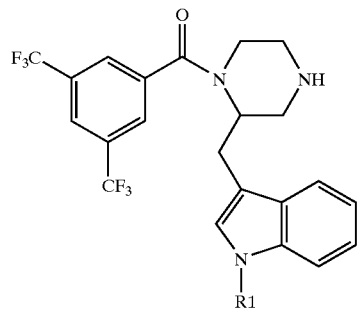

wherein R¹ has the above meaning, with a compound corresponding to formula III:

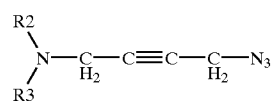

wherein R² and R³ have the above meanings, and wherein any reactive groups present are blocked by suitable protective groups, or
b) reacting a compound corresponding to formula IV:

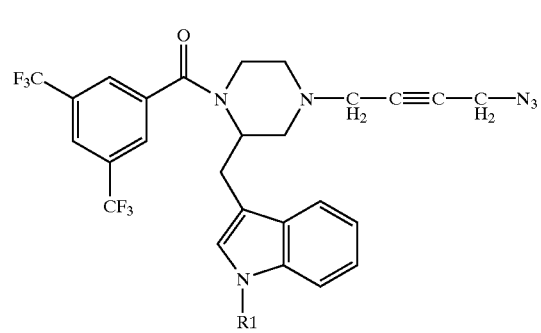

wherein R¹ has the above meaning, with a compound corresponding to formula V:

wherein R² and R³ have the above meanings, and wherein any reactive groups present are blocked by suitable protective groups, and
subsequently cleaving off any protective groups present therein, and
optionally converting a resulting compound of Formula I into a corresponding acid addition salt, or converting an acid addition salt into a free compound of Formula I.

* * * * *